United States Patent [19]

Patel et al.

[11] 4,085,616
[45] Apr. 25, 1978

[54] LIQUID MEASURING AND COLLECTION DEVICE

[75] Inventors: Bhupendra C. Patel, Elgin; Steven M. Boedecker, McHenry, both of Ill.

[73] Assignee: The Kendall Company, Boston, Mass.

[21] Appl. No.: 665,666

[22] Filed: Mar. 10, 1976

Related U.S. Application Data

[63] Continuation of Ser. No. 524,021, Nov. 15, 1974, abandoned.

[51] Int. Cl.² .................... G01F 1/00; G01F 23/00
[52] U.S. Cl. .......................... 73/215; 73/428; 128/2 F; 141/313; 141/331
[58] Field of Search .................. 73/215, 428; 33/126.7 R; 128/2 F, 295; 150/2.1, 8, DIG. 1; 141/313, 331, 332, 340

[56] References Cited

U.S. PATENT DOCUMENTS

| | | | |
|---|---|---|---|
| 48,256 | 6/1865 | Brown | 33/126.7 R X |
| 268,665 | 12/1882 | Hartwell | 141/331 |
| 426,667 | 4/1890 | Grissim | 141/331 X |
| 1,681,431 | 8/1928 | Pribil | 33/126.7 R |
| 2,136,043 | 11/1938 | Delaney | 150/2.1 |
| 2,648,981 | 8/1953 | Drake | 73/215 |
| 3,335,769 | 8/1967 | Ilg | 141/340 |
| 3,635,091 | 1/1972 | Linzer et al. | 128/295 |
| 3,859,854 | 1/1975 | Dye et al. | 73/215 |
| 3,871,230 | 3/1975 | Dye et al. | 73/215 |
| 3,871,231 | 3/1975 | Ciarico | 73/215 |
| 3,892,226 | 7/1975 | Rosen | 128/2 F |

*Primary Examiner*—James J. Gill
*Attorney, Agent, or Firm*—Powell L. Sprunger

[57] ABSTRACT

A device to measure and collect a liquid discharge comprising, an elongated indicating strip, a receptacle, and a container. The receptacle has a cavity to receive the discharge and means adjacent a lower end of the receptacle to retain the indicating strip in an upright position in the cavity. The container has a chamber and opening means in an upper end of the container to receive the discharge from the receptacle, and means for releasably attaching the container to the receptacle.

25 Claims, 7 Drawing Figures

U.S. Patent  April 25, 1978  4,085,616
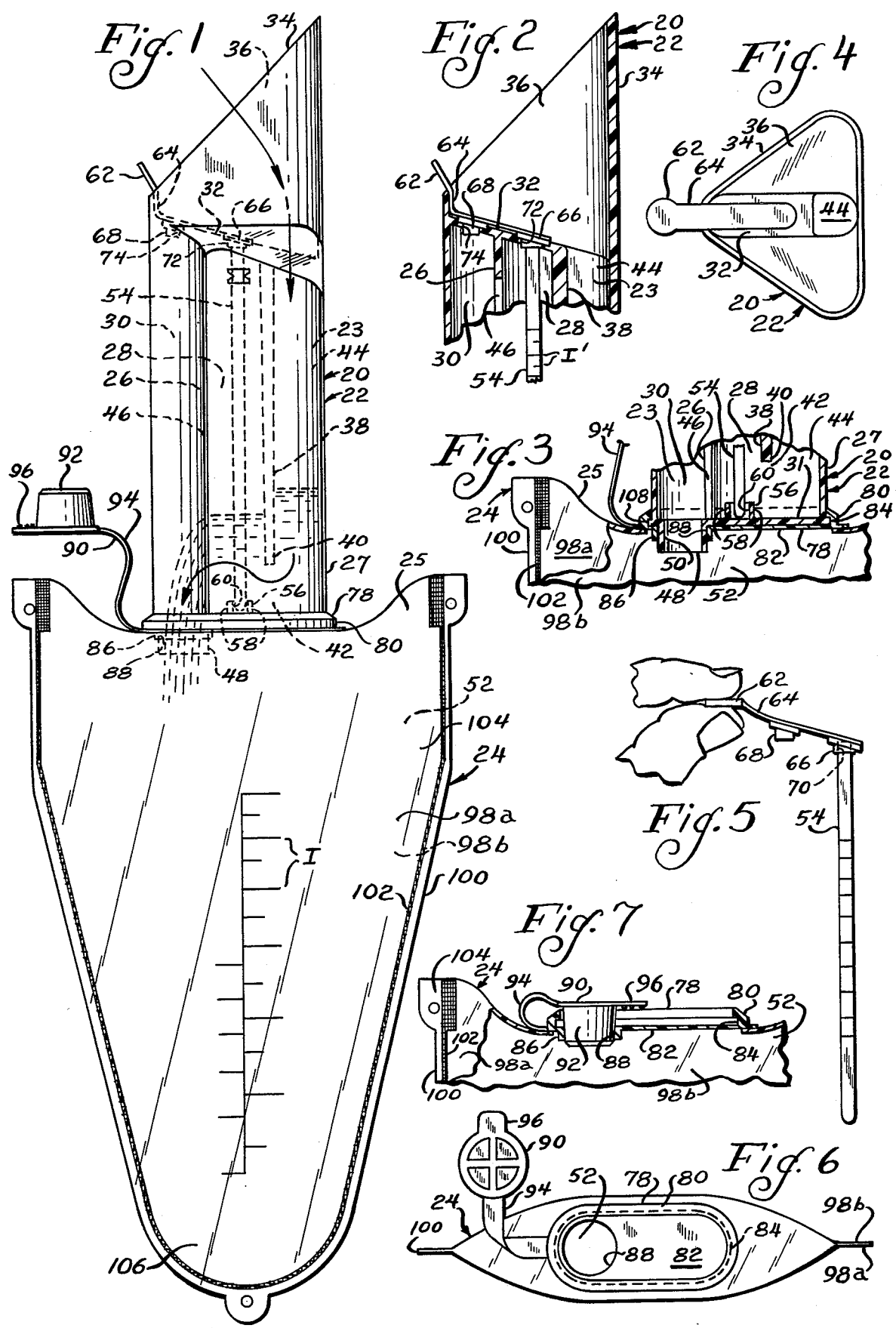

LIQUID MEASURING AND COLLECTION DEVICE

This is a continuation, of application Ser. No. 524,021 filed Nov. 15, 1974, now abandoned.

BACKGROUND OF THE INVENTION

The present invention relates to liquid receiving devices, and more particularly to devices for measuring and collecting a discharge of liquid.

In the past, it has been found desirable to obtain various data pertaining to a liquid discharge. In particular, it was discovered that many urological problems could be readily diagnosed by analyzing information obtained during the natural voiding of urine by patients. Presently, various types of devices are utilized to obtain data on the urine stream, such as total volume, average flow rate, force, velocity, and configuration of the stream.

Most of these devices have suffered from less than total reliability because they have required the presence of one or more observers while the patient is voiding. It is obvious that administration of such devices in this manner creates sufficient psychological difficulties for many of the patients to effect voiding. Consequently, if the patients void at all, the potentially erroneous data obtained may result in a false diagnosis and a loss of confidence in the device by the physician. A further complication arises from the fact that many of these devices are rather bulky, and somewhat difficult to use.

It is preferred that the flow measuring devices have a separate receptacle to receive and measure the urine discharge, and a lower container to receive the discharge from the receptacle, with the container being releasably attached to the receptacle. Accordingly, the receptacle may be cleared and sterilized for reuse, if desired, while the collected specimen of urine in the container may be retained for later diagnosis. If the receptacle is reused, it is desirable to use indicating means for the receptacle, if required, of simple and inexpensive construction, such that it may be readily replaced.

SUMMARY OF THE INVENTION

A principal feature of the present invention is the provision of a device of simplified construction for measuring and collecting a urine discharge, and which may be self-administered by a patient.

The device of the present invention comprises, an elongated indicating strip, a receptacle having a cavity and opening means to receive the discharge for passage into the cavity, and a container having a chamber and opening means in the upper end of the container communicating with the chamber. The receptacle has means for retaining a lower end of the indicating strip in the cavity, and port means adjacent a lower end of the receptacle for permitting passage of urine from the receptacle. The container has means for releasably attaching the container to the receptacle with the cavity of the container in communication with the port means of the receptacle.

Thus, a feature of the present invention is that the port means communicates with the chamber of the container for passage of urine from the receptacle into the chamber and collection therein.

Another feature of the invention is that the container may be readily attached to the receptacle for collecting the discharge in the container, and may be readily detached from the receptacle for subsequent analysis of the urine specimen.

A further feature of the invention is the provision of closure means for the opening means in the container for retention of the sample in the closed container.

Yet another feature of the invention is the provision of a depending extension from the receptacle to direct the urine discharge into the chamber of the container.

Still another feature of the invention is that the retaining means retains the indicating strip in an upright position in the receptacle cavity.

A feature of the invention is the provision of a retaining member which retains an upper end of the indicating strip in the receptacle cavity.

Another feature of the invention is that the indicating strip may be readily inserted into and withdrawn from the receptacle cavity for replacement of indicating strips in the receptacle.

Further features will become more fully apparent in the following description of the embodiments of this invention and from the appended claims.

DESCRIPTION OF THE DRAWINGS

In the drawings:

FIG. 1 is an elevational view of a liquid measuring and collecting device of the present invention, showing a lower container releasably attached to an upper receptacle;

FIG. 2 is a fragmentary sectional view of an upper end of the receptacle of FIG. 1;

FIG. 3 is a fragmentary elevational view, taken partly in section, of a lower end of the receptacle and an upper end of the container of FIG. 1;

FIG. 4 is a top plan view of the receptacle of FIG. 1;

FIG. 5 is an elevational view of a retaining member and an indicating strip which may be removably inserted into the receptacle of FIG. 1;

FIG. 6 is a top plan view of the container of FIG. 1; and

FIG. 7 is a fragmentary elevational view, taken partly in section, showing the upper end of the container of FIG. 1 with closure means received in opening means in the container.

DESCRIPTION OF THE PREFERRED EMBODIMENTS

Referring now to FIGS. 1–3, there is shown a device, generally designated 20, for measuring and collecting a discharge of liquid, such as urine. The device 20 includes a hollow receptacle designated generally 22 having a cavity 23, and a container designated generally 24 having an upper end 25 releasably attached to a lower end 27 of the receptacle 22. Preferably, the receptacle 22 is made from a suitable transparent material, such as plastic.

The receptacle 22, which has rounded end portions and an elongated central portion, has an upright wall 26 which extends laterally across the inside of the receptacle and which extends vertically the height of the receptacle. The upright wall 26 separates the inside of the receptacle into a compartment 28 and a channel or channel means 30. The lower end of the compartment 28 is closed by a bottom wall 31, while the upper end of the channel 30 and compartment 28 is partially covered by an upper wall 32.

As shown in FIGS. 1, 2, and 4, the receptacle 22 has an enlarged portion 34 adjacent the upper end of the receptacle defining an inlet port or opening means 36 to receive the incoming urine discharge, as indicated by the direction of the arrows in FIG. 1. The receptacle has a wall 38, as shown in FIGS. 1-3, extending laterally across the inside of the receptacle, and having a lower end 40 defining a space 42 intermediate the lower end 40 of the wall 38 and the lower or the bottom wall 31 of the receptacle. The wall 38 partially defines the compartment 28 and a passageway or passageway means 44 intermediate the wall 38 and an outer side wall of the receptacle 22. Thus, the urine discharge passes from the opening means 36 through the passageway means 44 and space 42 into the compartment 28.

As best shown in FIGS. 1-3, the wall 26 has an elongated vertical slot or opening means 46 communicating between the compartment 28 and the channel means 30 to permit passage of the liquid from the compartment to the channel means. As shown in FIGS. 1 and 3, the bottom wall 31 has a depending extension 48 defining port means 50 and directing liquid from the channel means 30 into a chamber 52 in the container 24, as will be further described below.

As shown in FIGS. 1-3, an indicating strip 54 is removably inserted into the compartment 28, with retaining means 56 adjacent the lower end 27 of the receptacle releasably receiving a lower end of the indicating strip 54. The retaining means 56 has a pair of bosses 58 extending from the bottom wall 31 into the cavity 23, with the bosses defining a slot 60 which receives the lower end of the strip 54 and assists in retaining the strip 54 in an upright position in the compartment 28.

As shown in FIG. 5, a retaining member 62 has an elongated flexible tab 64 having first and second spaced plugs 66 and 68, respectively, extending outwardly from one surface of the tab 64, with the first plug 66 being located adjacent one end of the tab 64, and the other plug 68 being located intermediate the plug 66 and the other end of the tab. The first plug 66 has a slot 70 to receive and retain an upper end of the indicating strip 54, as shown.

As illustrated in FIGS. 1 and 2, the upper wall 32 has a first opening or opening means 72 communicating with the compartment 28 to receive the indicating strip 54 and first plug 66, with the first opening 72 having dimensions to snugly engage the first plug 66. The upper wall 32 also has a second opening or opening means 74 extending through the wall to snugly receive the second plug 68. Thus, the first and second plugs 66 and 68 are removably received in the first and second openings 72 and 74 to releasably retain the tab 64 in place above the upper wall 32, while the first plug 66 assists in retaining the upper end of the indicating strips 54 in an upright position in the compartment 28. As shown in FIGS. 1, 2, and 4, the outer end of the tab 64 extends past the enlarged portion 34 to facilitate removal of the retaining member 62 from the receptacle 22.

The indicating strip 54 is sensitive to contact or wetting by liquid, such as urine, and provides an indication of the maximum height of liquid reached in the compartment 28 during the liquid discharge. Any suitable material may be utilized for the indicating strip 54, such as a material which changes color upon contact by the liquid. For example, a methylene blue compound or rhodamine may be utilized on the strip 54 to obtain the color contrast desired. Preferably, the indicating strip 54 is utilized a single time to measure the height of liquid in the compartment 28. Thus, the retaining member 62 permits easy placement and removal of indicating strips 54 in the receptacle 22. After removal of the strip, flow rate information may be determined by suitable indicia I' spaced along the strip. If desired, the strip 54 may be discarded after it has been removed and the information determined. Alternatively, if it is desired to keep the strip for a later reading, the other end of the tab 64 may be placed in a clip (not shown), or the second plug 68 may be positioned in an opening of a retaining device (not shown) to retain the strip until it is read. In either event, the retaining member 62 permits handling of the strip 54 in a sanitary manner without contacting the strip with the user's hands.

As shown in FIGS. 1, 3, 6, and 7, the container 24 has an upper resilient support member 78. The support member 78 has a resilient flange 80 extending peripherally around a wall 82 in the support member, with the flange 80 defining a peripherally extending slot 84. The support member 78 also has a depending flange 86 extending into the cavity 52 of the container 24 and defining an opening or opening means 88 having suitable dimensions to snugly engage the extension or tubular section 48 of the receptacle 22 when the container 24 is releasably attached to the lower end 27 of the receptacle 22, with the extension 48 passing through the flange 86.

The support member 78 also includes a closure 90 having a plug 92 attached to the support member 78 by a strap 94. The plug 92 is removably received in the opening means 88 of the support member 78, as shown in FIG. 7, with the flange 86 snugly engaging the plug 92 to close the opening means 88 and the cavity 52 of the container 24. The closure 90 also has a tab 96, as shown in FIGS. 1, 6 and 7, extending from the plug 92 to facilitate removal of the plug from the opening means 88.

The container 24 has a pair of flexible side walls 98a and 98b depending from the support member 78. The side walls are joined along their side edges 100 by suitable means, such as by a line of heat or radio frequency sealing 102 to close the side edges 100 of the side walls 98a and b and define the chamber 52 in the container 24. The side walls 98a and b may be made of any suitable material, preferably transparent, such as polyethylene. As shown in FIG. 1, the side wall 98a has a plurality of vertically spaced indicia I to measure the volume of liquid collected in the chamber 52. In a preferred embodiment, the container 24 has and enlarged portion 104 adjacent the upper end of the container 24 which is tapered to a lower portion 106 of the container of reduced width to obtain a more accurate determination of liquid volume by the indicia I when a relatively small volume of urine has been collected in the container 24.

As shown in FIG. 3, the bottom wall 31 of the lower end 27 of the receptacle 22 has an outwardly directed flange 108 extending peripherally around the receptacle. The container 24 is releasably attached to the lower end 27 of the receptacle 22 by inserting the extension 48 through the opening means 88 in the support member 78, and by pressing the support member 78 against the lower end 27 of the receptacle 22, such that the resilient flange 80 of the support member 78 passes over and releasably locks against the flange 108 of the receptacle 22, with the receptacle flange 108 being received in the slot 84 defined by the flange 80. In this configuration, the wall 82 of the support member 78 mates against the bottom wall 31 of the receptacle 22. The container 24 is removed from the receptacle 22 by pulling the container relative the receptacle, such that the flange 80 of the support member 78 passes over and disengages from the flange 108 of the receptacle 22.

In use of the device, the plug 92 of the closure 90 is removed from an opening means 88 of the support member 78, and the support member 78 of the container 24 is attached to the lower end 27 of the receptacle 22, as previously described. The port 36 of the receptacle 22 is then positioned by a patient in privacy to receive the discharge of urine. As the liquid discharge passes into the enlarged portion 34 of the receptacle, the enlarged portion directs the discharge into the passageway 44 for collection in the receptacle. As the discharge continues, the liquid collects in the lower part of the compartment 28 and passes from the compartment 28 through the slot 46 into the channel 30. From the channel, the liquid passes through the port means 50 in the extension 48 into the chamber 52 of the container 24. As the rate of discharge into the receptacle increases, the height of liquid in the compartment 28 also increases while the liquid also drains through the slot 46 into the channel 30.

For a given rate of flow of the discharge into the receptacle the liquid attains a fixed height in the compartment 28, and the liquid passes at a fixed rate of flow through the slot 46. Hence, if the rate of flow of the liquid discharge into the receptacle increases, the height of liquid in the compartment raises an additional amount, and the rate of flow through the slot 46 also increases, since the liquid flows through a larger vertical portion of the slot 46. Thus, as long as the rate of flow of the discharge into the receptacle increases, the height of liquid in the compartment 28 continues to rise, and the rate of flow of liquid through the slot 46 also increases. When the flow rate of the incoming discharge abates, the liquid drains from the compartment 28 into the channel 30 faster than it enters the compartment, and the height of the liquid in the compartment begins to subside.

Peak flow rate of the incoming liquid discharge may be defined as the maximum rate of flow of the discharge. Since the height of liquid in the compartment raises or lower responsive to an increase or decrease, respectively, of the flow rate of the incoming discharge, it is apparent that the maximum height of liquid attained in the compartment during the discharge serves as an indication of the approximate peak flow rate of the discharge. Although anomalies in the discharge, such as a momentary surge of the discharge, may not be ultimately reflected in the maximum liquid height in the compartment, due, in part to the leg between the time the discharge enters the receptacle and the time it enters the compartment, the device determines the peak flow rate with sufficient accuracy for such purposes as are under discussion. In particular, a urine stream during voiding has a relatively slow rate of change of flow rate, and the device of the present invention indicates a peak flow rate for the discharge which is sufficiently accurate for purposes of diagnosing the patient.

It is possible that the approximate peak flow rate of the urine discharge may be determined by observing the highest level of liquid accumulated in the compartment 28 during the discharge. Direct reading by the patient may be impractical or difficult during self-administration of the apparatus as thus far described, if the apparatus is utilized to collect a discharge of liquid during voiding, and it is desirable that the device be self-administered by the patient in order to alleviate any psychological problems of the patient which might be caused by observation of the receptacle during voiding.

Accordingly, the indicating strip 54 has been provided to automatically record the approximate maximum height of liquid collected in the compartment 28 during the liquid discharge. After the liquid discharge has been completed, a direct reading of the approximate peak flow rate may be determined by the indicia I', as shown in FIG. 2, either before or after removal of the indicating strip 54 from the receptacle 22. Alternatively, the indicia I' may be placed on the wall of a transparent receptacle 22.

It is apparent that the rate of drainage from the compartment 28 into the channel 30 is partly dependent upon the precise structure of the receptacle 22. For example, although the slot 46 is shown as having parallel sides, it is contemplated that the slot may be widened or narrowed at desired vertical positions to increase or decrease the flow rate of liquid through the wall in that area, and the wall 26 may have a plurality of slots or openings if desired. Also, the cross sectional area of the compartment 28 itself may be selected of a suitable size to provide the desired sensitivity of liquid column height for a more accurate determination of the peak flow rate.

It is contemplated that a particular structure for the receptacle would first be established, dependent on the accuracy desired and the expected range of values for the peak flow rate of the liquid discharge. Next the receptacle could be calibrated against known constant flow rates of a discharge passing into the receptacle to determine the appropriate location for the indicia I' on the strip. That this may be readily accomplished is apparent from the fact that the peak flow rate for a discharge having a constant flow rate is the value of the constant flow rate itself. Accordingly, when the discharge of constant flow rate is directed into the receptacle, liquid rises in the compartment to a level at which liquid entering the compartment is offset by the liquid draining from the compartment into the channel, and the receptacle or strip is marked at this height for peak flow rate by the value of the flow rate of the constant discharge.

As noted above, once the rate of flow of the liquid discharge into the receptacle abates, the height of the liquid in the compartment 28 subsides, and the approximate peak flow rate has already been determined on the indicating means or strip 54. During the remainder of the liquid discharge, the liquid continues to drain from the compartment 28 into the channel 30 until the discharge is terminated and drainage from the compartment to the channel eventually stops. Since the liquid drains from the channel 30 of the receptacle 22 into the container 24, the volume of liquid which collects in the container 24 during the liquid discharge may readily be determined by the indicia I on the container 24, as shown in FIG. 1.

Since the patient may use the device without observation, unnatural voiding or failure to void which normally occur from psychological difficulties when a patient voids under observation is prevented. After voiding, the patient merely summons the physician or nurse, who then uses the device to diagnose the patient's voiding. As previously indicated, the indicating strip 54 may be removed from the receptacle to obtain a reading of the peak flow rate of the urine discharge by use of the indicia I' on the strip 54, or the strip may be retained for latter use if desired. The container 24 may be removed from the receptacle 22 to obtain a specimen of urine from the chamber 52 of the container 24 through the opening means 88. Alternatively, the plug 92 of the closure 90 may be placed in the opening means 88 to close the opening means and cavity 52 of the container 24, and the specimen may be retained for later use, if desired. In either event the closed container 24 may be discarded in a sanitary manner after removal from the receptacle 22. The receptacle 22 may be cleaned and sterilized for future use with a different indicating strip 54, to reduce the cost of diagnosing various patients.

The foregoing detailed description is given for clearness of understanding only, and no unnecessary limitations should be understood therefrom, as modifications will be obvious to those skilled in the art.

We claim:

1. A device to measure and collect a discharge of urine, comprising:
    an elongated indicating strip;
    a receptacle having a cavity, a back wall, a hollow urine receiving portion adjacent an upper end of the receptacle, first opening means communicating with said urine receiving portion to receive the discharge for passage into the cavity, an upper wall defining an upper part of said cavity and a lower part of the urine receiving portion and having second opening means communicating between said cavity and said urine receiving portion to receive said strip, said upper wall extending from said first opening means to third opening means communicating with said cavity adjacent said back wall, said receptacle having a lateral lower wall having means for retaining a lower end of the indicating strip in the cavity, and port means permitting passage of urine from the receptacle; and
    a container having a chamber, opening means in the upper end of the container communicating with the chamber, and means for releasably attaching the container to the receptacle with said chamber of the container in communication with the port means of the receptacle through the opening means of the container to receive urine from the receptacle throgh the port means into said chamber.

2. A device to receive a discharge of urine, comprising:
    a receptacle having a cavity to receive and measure the discharge, a transverse lower wall having a lower surface and defining a lower part of said cavity, a hollow extension depending below said lower wall and defining port means to direct passage of urine from the receptacle, and means for measuring a characteristic of said discharge associated with flow of the discharge in said cavity; and
    a container having a chamber, a relatively rigid transverse upper wall for placement in closely spaced facing relationship adjacent said lower surface of said lower wall and having opening means to receive said extension, and means for releasably attaching the container directly to the receptacle and for supporting the container from the receptacle with the extension received through the opening means into said chamber, whereby urine is directed through the port means in said extension to the chamber of the container for collection therein.

3. The device of claim 2 wherein said extension comprises a tubular section, and said opening means has a circular shape, with said opening means having an inside diameter approximately equal to the outside diameter of said extension.

4. The device of claim 3 wherein said upper wall has a depending flange extending at least partially around the periphery of the opening means and snugly engaging the extension when said container is attached to the receptacle.

5. A device to receive a discharge of urine, comprising:
    a receptacle having a cavity to receive and measure the discharge, and a port means adjacent a lower end of the receptacle and communicating with the cavity to permit passage of urine from the receptacle; and
    a container having a chamber, a relatively rigid upper wall for placement in facing relationship adjacent a lower surface of said receptacle and having opening means extending through the upper wall adjacent an upper end of the container and communicating with the chamber, means for releasably attaching the container directly to the receptacle with the port means in communication with said chamber to receive urine from the receptacle into said chamber, and plug means for releasably closing said opening means, whereby the opening means may be closed by the plug means after removal of the container from the receptacle, and a depending flange extending at least partially around the periphery of the opening means to snugly engage the plug when it is received in the opening means.

6. The device of claim 5 wherein said plug means comprises a plug removably received in said opening means.

7. The device of claim 6 including a strap connecting the plug to the upper end of the container.

8. The device of claim 6 wherein said plug includes a tab to facilitate removal of the plug from the opening means.

9. A device to receive a discharge of urine, comprising:
    a receptacle having a cavity to receive the discharge, a bottom wall, port means adjacent a lower end of the receptacle and communicating with the cavity to permit passage of urine from the receptacle, and flange means adjacent the lower end of the receptacle, said receptacle flange means comprising an outwardly directed flange extending at least partially around the receptacle adjacent the lower end of the receptacle; and
    a container having a chamber, opening means adjacent an upper end of the container communicating with the chamber, an upper wall, the flange means cooperating with the flange means on the receptacle to releasably attach the container to the receptacle with said upper wall mating against the bottom wall of the receptacle, and with the port means communicating with the chamber, said container flange means comprising a resilient flange member defining an inwardly directed slot to receive and snap-fit on said flange, with said flange member releasably locking over the flange when the container is attached to the receptacle, whereby urine passes from the cavity to the chamber for collection therein.

10. The device of claim 9 wherein said flange comprises an outwardly directed extension of the bottom wall.

11. The device of claim 9 wherein the flange extends completely around the periphery of the receptacle, and the flange member extends completely around the flange when the container is attached to the receptacle.

12. The device of claim 9 wherein said bottom and upper walls have approximately the same outer dimensions.

13. The device of claim 12 wherein said bottom and upper walls have rounded ends and an elongated central portion.

14. The device of claim 9 wherein the opening means extends through said upper wall.

15. A container for receiving a liquid discharge, comprising:
 a liquid measuring receptacle;
 an upper relatively rigid, resilient support member having a wall defining an upper portion of the container, a resilient retaining flange extending upwardly from the wall, with said flange having means for releasably attaching the support member directly to said receptacle, and opening means extending through the wall intermediate spaced portions of the flange;
 a plug removably received in the opening means to close the opening means;
 a strap connecting the plug to an upper portion of the container; and
 a pair of flexible sidewalls depending from the support member and defining a chamber communicating with the opening means.

16. The container of claim 15 wherein said flange extends at least partially around the periphery of said wall.

17. A container for receiving a liquid discharge comprising, a receptacle having opening means adjacent an upper end of the receptacle, relatively rigid lateral support means adjacent the upper end of the receptacle, said support means having an elongated wall extending laterally across an upper part of the receptacle and defining said opening means, with said wall having an upwardly directed flange defining an inwardly directed retaining slot, and a pair of flexible side walls joined along their sides and defining a tapered configuration from the upper to lower ends of the receptacle, with said side walls depending from the support means, and said side walls defining a chamber communicating with said opening means.

18. A device for receiving and measuring a urine discharge, comprising:
 an elongated wettable indicating strip;
 a receptacle having side walls defining a cavity, first opening means adjacent an upper end of the receptacle and communicating with the cavity to receive the discharge, means for measuring a dynamic characteristic of said discharge, second opening means adjacent the upper end of the receptacle to receive the indicating strip in said cavity with an intermediate portion of the strip in a spaced relationship from said side walls, a bottom wall extending laterally in the receptacle and having means for releasably retaining a lower end of said strip to maintain the strip in an upright position in said cavity and in said spaced relationship exposed to contact by said discharge, and means for releasably covering the second opening means and for retaining an upper end of said strip in said cavity.

19. The device of claim 18 wherein the retaining means comprises a pair of spaced bosses extending from the bottom wall into said cavity, said bosses defining slot means to receive the lower end of said strip.

20. The device of claim 18 wherein said receptacle includes first and second walls defining a compartment in which said strip is received.

21. The device of claim 20 wherein said first wall is spaced from the bottom wall and defines passageway means with a wall portion of the receptacle, said passageway means communicating between the first opening means and with said compartment, and in which said second wall defines channel means with a wall portion of the receptacle, said channel means communicating with the compartment through opening means in the second wall and communicating with port means adjacent the lower end of the receptacle through which urine passes out of the receptacle.

22. A device for receiving and measuring a urine discharge, comprising
 an indicating strip;
 a receptacle having a cavity and first opening means communicating with the cavity for receiving the discharge, and second opening means extending through an upper wall of the receptacle to said cavity; and
 a retaining member having a first plug means removably and snugly received in said second opening means of the upper wall and having means for releasably retaining an upper end of said strip, and said retaining member having an elongated flexible tab extending from said plug means to facilitate removal of the first plug means from the second opening means.

23. The device of claim 22 wherein the retaining means comprises slot means extending from an end of the first plug means to receive and engage the upper end of said strip.

24. The device of claim 13 wherein the upper wall includes third opening means spaced from the second opening means, and said retaining member includes second plug means spaced from the first plug means, said second plug means being removably received in the third opening means.

25. Indicating means, comprising:
 an indicator strip; and
 a flexible retaining member having an elongated tab, a first plug adjacent one end of the tab and extending outwardly from one surface of the tab, said first plug having a slot to receive one end of said strip, and said retaining member having a second plug extending outwardly from said one surface intermediate the first plug and the other end of the tab.

* * * * *

UNITED STATES PATENT AND TRADEMARK OFFICE
CERTIFICATE OF CORRECTION

PATENT NO. : 4,085,616
DATED : April 25, 1978
INVENTOR(S) : Bhupendra C. Patel and Steven M. Boedecker It is certified that error appears in the above-identified patent and that said Letters Patent are hereby corrected as shown below:

In column 1, line 36, "cleared" should be -- cleaned --

In column 5, line 51, "leg" should be -- lag -- .

In column 6, line 68, "latter" should be -- later -- .

In column 7, line 43, "throgh" should be -- through --

In column 8, line 53, "the", second occurrence, should be -- and -- .

Signed and Sealed this

Twenty-ninth Day of August 1978

[SEAL]

Attest:

RUTH C. MASON
Attesting Officer

DONALD W. BANNER
Commissioner of Patents and Trademarks